(12) United States Patent
McMahon et al.

(10) Patent No.: US 10,098,530 B2
(45) Date of Patent: Oct. 16, 2018

(54) MEDICAL DIAGNOSTIC INSTRUMENT

(71) Applicant: Welch Allyn, Inc., Skaneateles Falls, NY (US)

(72) Inventors: Michael T. McMahon, Syracuse, NY (US); Adam P. Vallee, Cato, NY (US); Richard A. Tamburrino, Auburn, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 519 days.

(21) Appl. No.: 14/935,838

(22) Filed: Nov. 9, 2015

(65) Prior Publication Data

US 2016/0128555 A1     May 12, 2016

Related U.S. Application Data

(60) Provisional application No. 62/076,761, filed on Nov. 7, 2014.

(51) Int. Cl.
    *A61B 1/227*          (2006.01)
    *A61B 1/00*           (2006.01)

(52) U.S. Cl.
    CPC .......... *A61B 1/2275* (2013.01); *A61B 1/0011* (2013.01); *A61B 1/00032* (2013.01); *A61B 1/00052* (2013.01); *A61B 1/00071* (2013.01); *A61B 1/00108* (2013.01); *A61B 1/00188* (2013.01); *A61B 1/00195* (2013.01)

(58) Field of Classification Search
    CPC .............................. A61B 1/227; A61B 1/2275

USPC ......................................................... 600/200
See application file for complete search history.

(56) References Cited

U.S. PATENT DOCUMENTS

| | | | | |
|---|---|---|---|---|
| 3,384,076 | A | * | 5/1968 | Speelman ............... A61B 1/227 |
| | | | | 313/318.01 |
| 3,728,998 | A | * | 4/1973 | Heine ..................... A61B 1/227 |
| | | | | 385/117 |
| 3,934,578 | A | * | 1/1976 | Heine ..................... A61B 1/227 |
| | | | | 313/318.01 |
| 4,147,163 | A | | 4/1979 | Newman et al. |
| 4,366,811 | A | * | 1/1983 | Riester ................... A61B 1/227 |
| | | | | 600/200 |
| 4,380,998 | A | * | 4/1983 | Kieffer ................. A61B 1/2275 |
| | | | | 128/864 |
| 4,643,171 | A | * | 2/1987 | Riester ..................... A61B 1/07 |
| | | | | 600/200 |
| 5,658,235 | A | * | 8/1997 | Priest ..................... A61B 1/042 |
| | | | | 600/112 |
| 6,106,457 | A | | 8/2000 | Perkins et al. |
| 6,142,934 | A | * | 11/2000 | Lagerway .......... A61B 1/00041 |
| | | | | 600/200 |
| 7,029,439 | B2 | * | 4/2006 | Roberts .................. A61B 1/227 |
| | | | | 600/178 |

(Continued)

*Primary Examiner* — Eric S Gibson

(57) ABSTRACT

A handheld diagnostic instrument includes a handle and an instrument head associated with the handle. An innerformer is disposed in an inner cavity of the instrument head in which the instrument head further includes a tab holder. A cushion member is disposed within the housing between the innerformer and the interior of the instrument head. Further, a lens is attached to the instrument head, the lens including a lens tab. A seal is formed between the lens and the innerformer when the lens tab is engaged with the tab holder wherein the cushion member acts to bias the innerformer to maintain the defined seal.

20 Claims, 12 Drawing Sheets

(56) References Cited

U.S. PATENT DOCUMENTS

| | | | |
|---|---|---|---|
| 7,399,275 B2 | 7/2008 | Goldfain et al. | |
| 7,670,287 B2* | 3/2010 | Roberts | A61B 1/227 600/178 |
| 7,803,110 B2* | 9/2010 | Goldfain | A61B 1/00188 600/112 |
| 9,579,014 B2* | 2/2017 | Eder | A61B 1/2275 |
| 2004/0039251 A1* | 2/2004 | Roberts | A61B 1/227 600/178 |
| 2006/0129031 A1* | 6/2006 | Roberts | A61B 1/227 600/131 |
| 2014/0336467 A1* | 11/2014 | Eder | A61B 1/2275 600/200 |
| 2016/0128555 A1* | 5/2016 | McMahon | A61B 1/2275 600/200 |

* cited by examiner

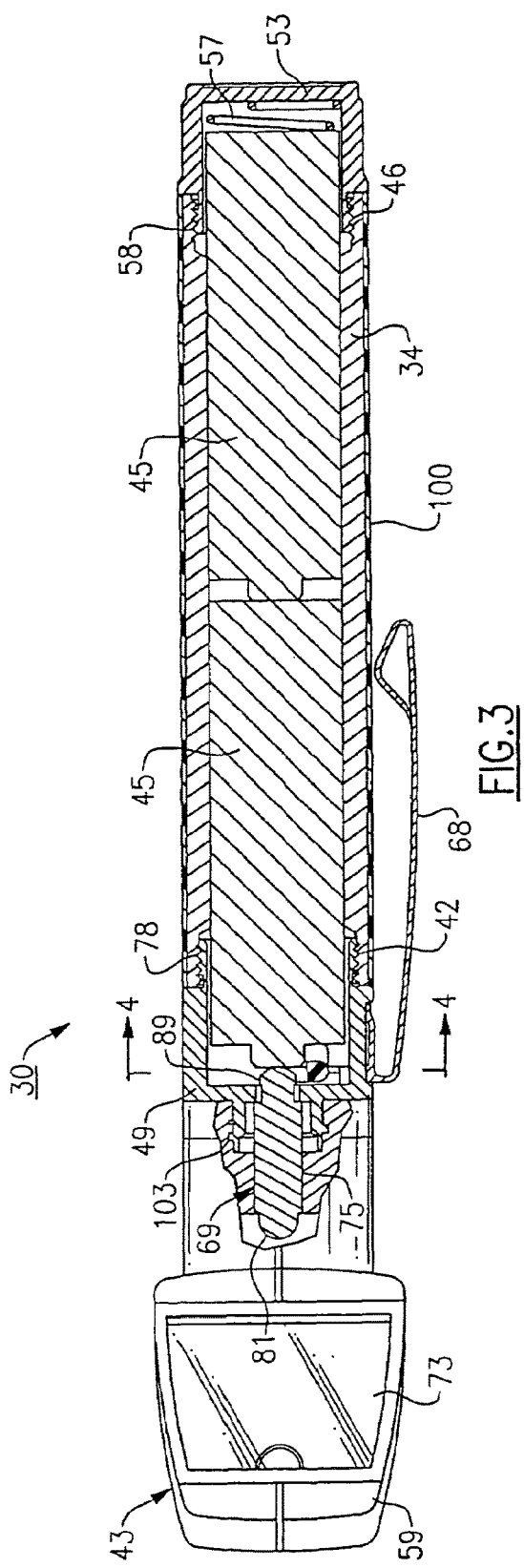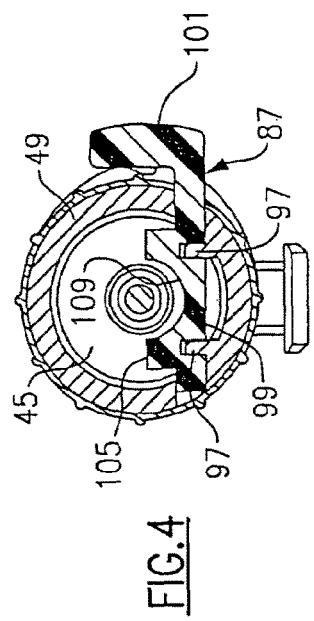

MEDICAL DIAGNOSTIC INSTRUMENT

CROSS REFERENCE TO RELATED APPLICATIONS

This application claims priority under relevant portions of 35 U.S.C. § 119 to U.S. Patent Application No. 62/076,761, filed Nov. 7, 2014 and entitled: Medical Diagnostic Instrument. The entire contents of this referenced application is herein incorporated by reference.

BACKGROUND

This disclosure relates generally to medical diagnostic instruments, such as ophthalmoscopes and otoscopes. For example, a number of known instrument designs, such as those manufactured by Welch Allyn Inc., of Skaneateles Falls, N.Y., are detailed in U.S. Pat. Nos. 6,106,457, 7,029,439, 7,399,275, and 7,670,287, each of which are incorporated herein by reference in their entirety.

Otoscopes can include a port that enables caregivers, such as clinicians, to insufflate the ear of a patient in order to provide a more complete diagnostic examination. An example of a known pneumatic otoscope 400 is partially depicted in FIG. 11, including an instrument head 404 that includes an attachment end 408 that is securable to a handle (not shown). The instrument head 404 is defined by a hollow interior and includes a distal end that retains a distal insertion portion 410 (partially shown) that is shaped and configured to support a speculum tip element 412, the latter being insertable to a predetermined distance within the ear canal (not shown) of a patient. At the opposing rear or proximal end of the instrument head 404, a viewing lens 416 is pivotally attached to the instrument head 404 at an upper end via a connection 424, the viewing lens 416 including a lens tab 428 extending from a lower or bottom end. The viewing lens 416 forms a seal with the interior of the instrument head 404 wherein the viewing lens 416 can also include a peripheral bumper 418. A insufflation port 420 extends into the interior of the instrument head 404 wherein a pneumatic bulb (not shown) and hose (not shown) can be fluidically connected to the insufflation port 420. Squeezing the pneumatic bulb enables air under pressure to be directed to the ear of the patient.

Successful pneumatic otoscopy requires a sealed innerformer. A typical innerformer is disposed within the interior of the instrument head and serves to support the distal insertion portion and further enables optical fibers from a contained illumination assembly to be directed to the exterior of the distal insertion portion. Leaks developed in the instrument can prevent adequate pressurization. Without proper pressurization, the ear drum will not deflect as intended and the user may thus misdiagnose fluid behind the ear when in fact it does not exist. In the case of some leaks, the user may hear air hissing from the device and try to compensate with ever more vigorous hand pumping. These quick blasts do not allow adequate pressure modulation and in fact can injure the delicate ear drum.

Prior art otoscopes tend to suffer from leaks, either at the time of manufacturing or after a period of use. Leaks occur for many reasons, but among the most common is a poor seal between an interface defined between the viewing lens at the proximal end of the instrument head and the mating innerformer surface. This interface has a large perimeter that presents many opportunities for air to escape the instrument. If either the viewing lens or the innerformer deviates from flat surface to surface contact, an air passage can result along at least a portion of the periphery of the lens and the innerformer. One possible solution would be to manufacture these parts with extremely high tolerances. This solution would drastically increase the overall cost of the assembly and also increase the number of components that would have to be discarded in order to meet the higher tolerance thresholds. Still further, nicks, scratches or other manufacturing defect on either surface (the rear of the innerformer assembly and the interior periphery of the lens) would produce the same deleterious effect. While these problems may not exist at the time of manufacture, even with high tolerance manufacture, these problems could easily result over time and use of the instrument based subjecting the instrument to shock or impact loads (e.g., drops), the usual sliding motion of the lens relative to the innerformer to effect instrumentation, and other use case scenarios.

More specifically, a drop may produce gross deflection of the innerformer within the instrument head, thereby moving the rear surface relative to the interior peripheral contacting lens surface. This dynamic motion of one component relative to the other can scratch or otherwise damage the sealing surfaces. Otoscopic instruments that do not protect the innerformer from impact forces are especially vulnerable to this latter issue.

The above noted sealing interface between the lens and the rear surface of the innerformer may also leak if the lens retention means of the instrument applies inadequate or unbalanced forces to the lens. Insufficient restraining forces allow air pressure to push the lens away from the innerformer. As a result, airleaks are produced from the resulting gap. Similarly, an unbalanced restraining force may tip the lens such that one peripheral section lifts off or away in relation to the sealing interface. As a result, the section that is lifted away also becomes prone to undesired air leakage. This latter situation can arise at the time of manufacturing due to tolerance variations, but this undesired situation may also occur because the various components warp or otherwise migrate or creep over time and changes in environmental exposure.

Other than creating a higher degree of tolerancing, an alternative technique applied in some prior art otoscopes to effectuate a proper seal is the addition of an elastomeric sealing member disposed at the above-defined interface. While employing an elastomeric seal can provide an airtight junction, this proposed solution requires the added expense of the elastomeric component, as well as other parts or features that become necessary in order to constrain the elastomeric part. Elastomeric parts can also tear or wear away (erode) when the pivoting lens repeatably slides over them in use. Further, elastomeric compounds used in the manufacture of sealing members (e.g., O-rings) can degrade with time and temperature or exhibit a residual adhesion effect (i.e., 'stiction'), whereby the elastomeric components adhere to the lens over time and rip away or are otherwise rendered unsuitable for providing an adequate air seal with the interior of the instrument head when the user finally slides the lens

BRIEF DESCRIPTION

According to one aspect, a diagnostic instrument is provided that comprises a handle and an instrument head associated with the handle, the instrument head comprising a housing that includes a tab holder. An innerformer is disposed in an inner cavity of the instrument head, as well as a cushion member disposed between the innerformer and the interior of the housing in addition to a lens attached to the instrument head, the lens including a lens tab. A seal is formed between the lens and the innerformer when the lens tab is engaged with the tab holder.

In addition, the diagnostic instrument may also include an insufflation port on a portion of the housing wherein a gap or spacing is defined between at least a portion of the innerformer and the interior of the instrument head. The gap or spacing enables the innerformer to "float" such that the cushion member creates a bias that maintains the seal between the innerformer and the viewing lens and more specifically between a rear surface of the innerformer and a peripheral surface of the viewing lens. The seal is effectively maintained while pressure is applied to the interior of the instrument head through the insufflation port.

In at least one version, a light source such as an LED is also included as part of one of or both of the handle and the instrument head. In at least one version, the LED is integrated directly into the instrument head.

According to another aspect, a method of manufacturing a handheld diagnostic instrument is provided. The method includes providing a handle and an instrument head associated with the handle. An innerformer is disposed in an inner cavity of the instrument head along with a cushion member that is disposed between the innerformer and the housing. According to this method, a viewing lens is further provided that is attached to the instrument head, the viewing lens including a lens tab. A seal is formed between the viewing lens and the innerformer when the lens tab is engaged with a tab holder of the instrument head.

According to one version, a light source such as an LED is associated with at least one of the handle and the instrument head. The LED can be integrated within the instrument head. A gap is formed between the innerformer and the interior of the instrument head. This gap enables the innerformer in combination with the cushion member to create a bias against the seal formed between the viewing lens and the innerformer when the lens tab is engaged with the tab holder. This seal can be maintained when pressure is added pneumatically to the interior of the instrument head using an insufflation port provided on the instrument head.

According to yet another aspect, a method of conducting pneumatic otoscopy with a handheld otoscope is provided. The method includes providing an otoscope. The otoscope includes an instrument head associated with the handle, the instrument head having a housing, wherein the housing comprises a tab holder. The otoscope further includes an insertion portion at a distal end of the instrument head, an innerformer disposed in an inner cavity of the instrument head, a cushion member disposed between the innerformer and the housing, and a viewing lens attached to the instrument head. The viewing lens includes a lens tab, wherein a seal is formed between the lens and the innerformer when the lens tab is engaged with the tab holder. The method further includes inserting the insertion portion into an ear canal of a patient and inserting a gas into the inner cavity of the instrument head through an insufflation port located on a portion of the instrument head. The gas passes through the inner cavity, through the insertion portion, and to the ear canal.

BRIEF DESCRIPTION OF THE DRAWINGS

Figure 1:
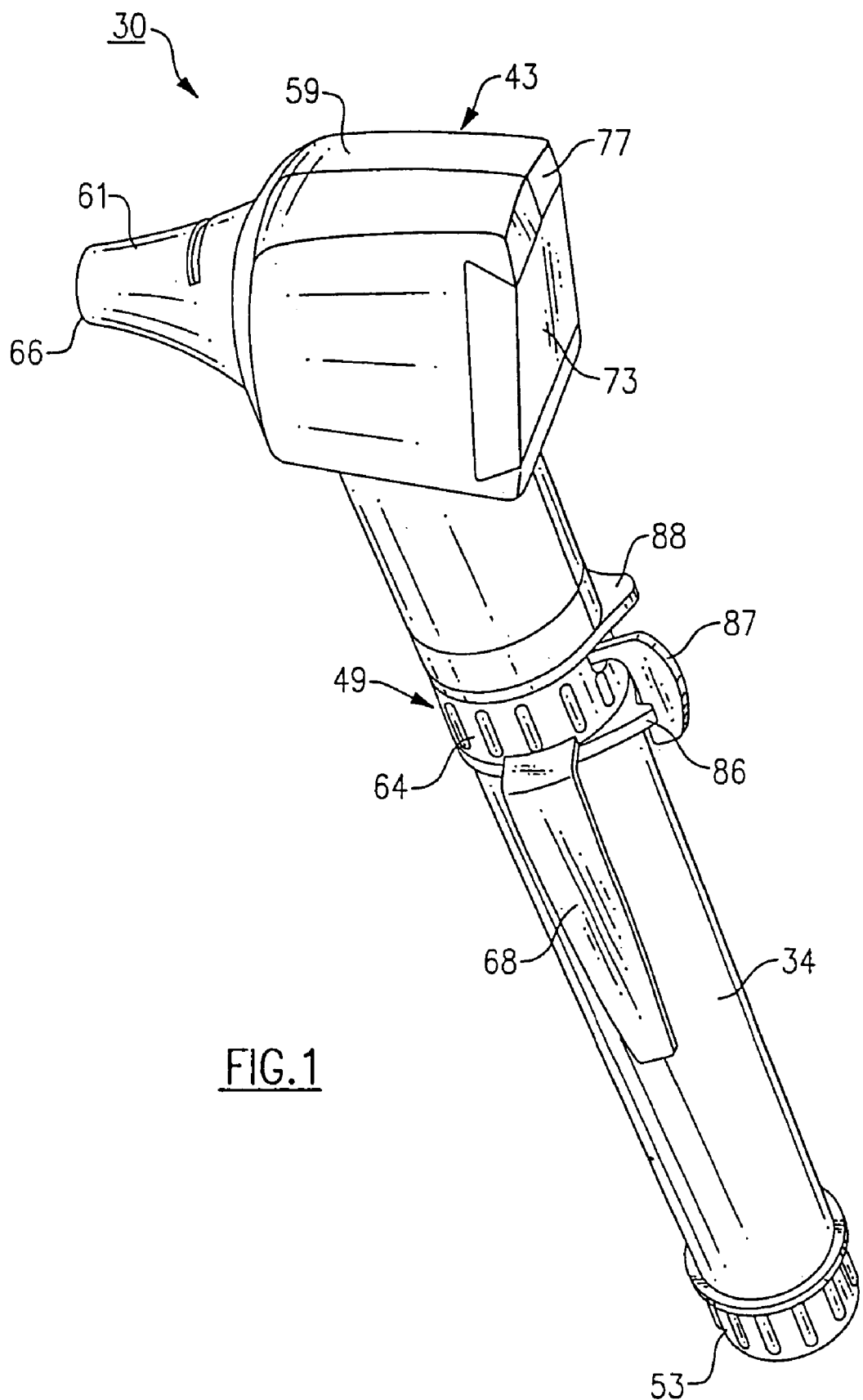
Figure 2:
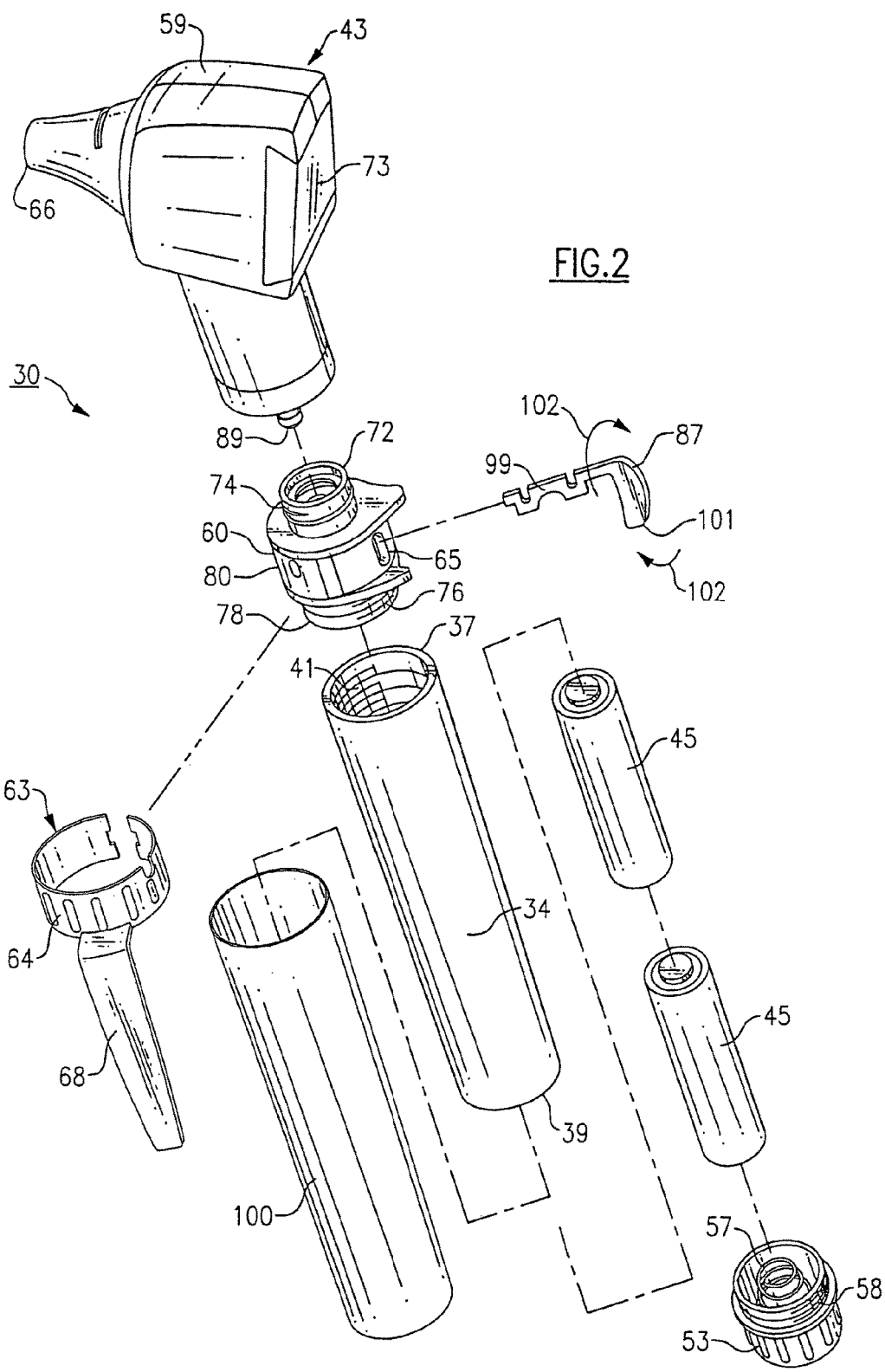
Figure 5:
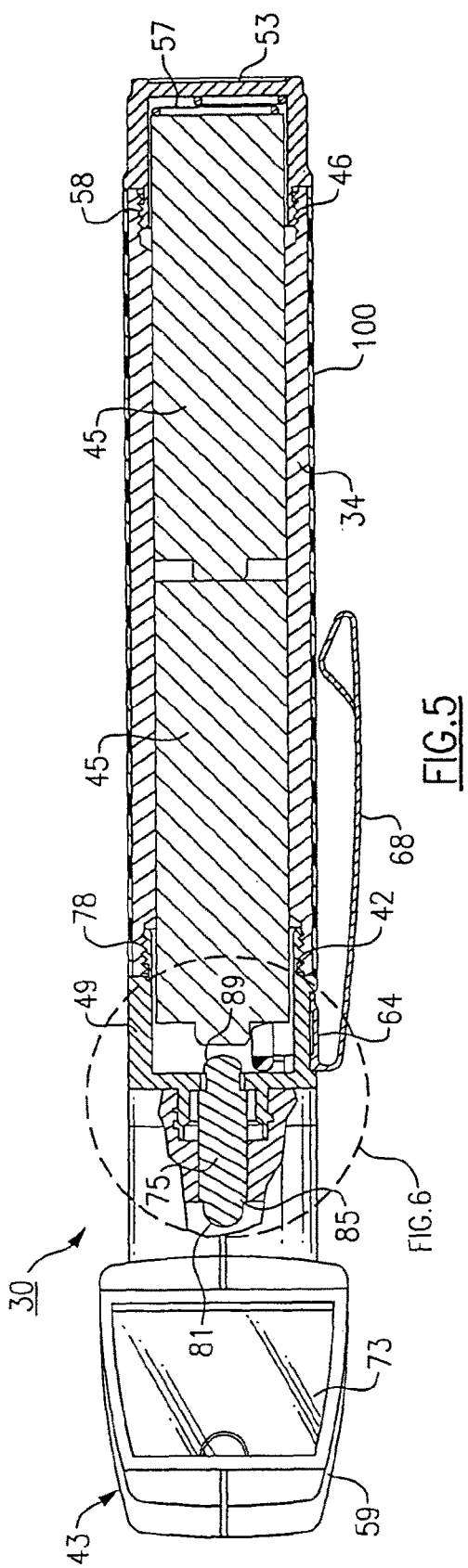
Figure 6:
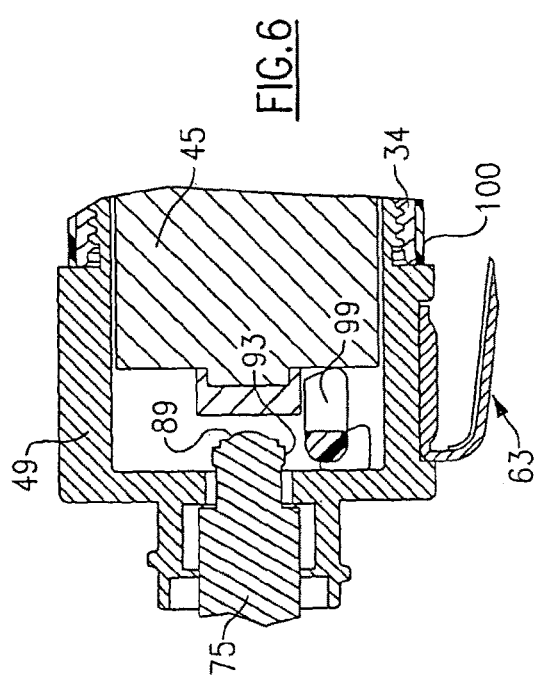
Figure 7:
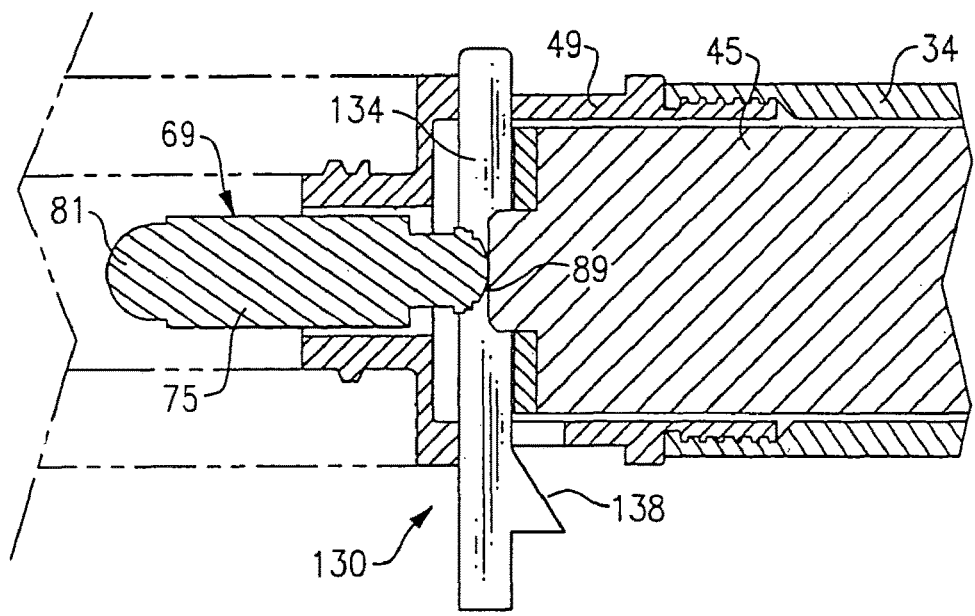
Figure 8:
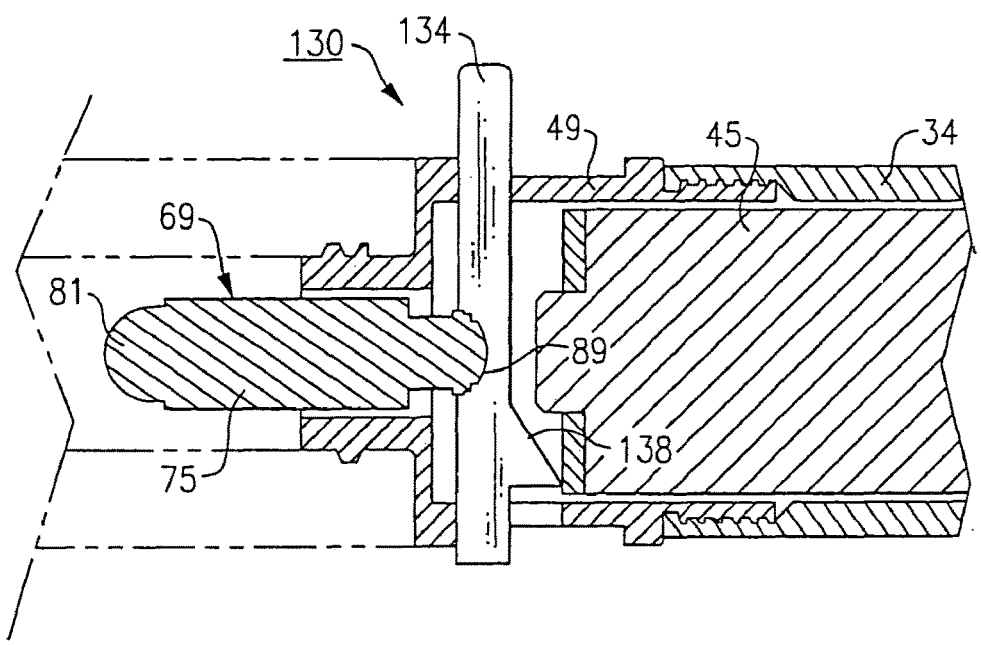
Figure 9:
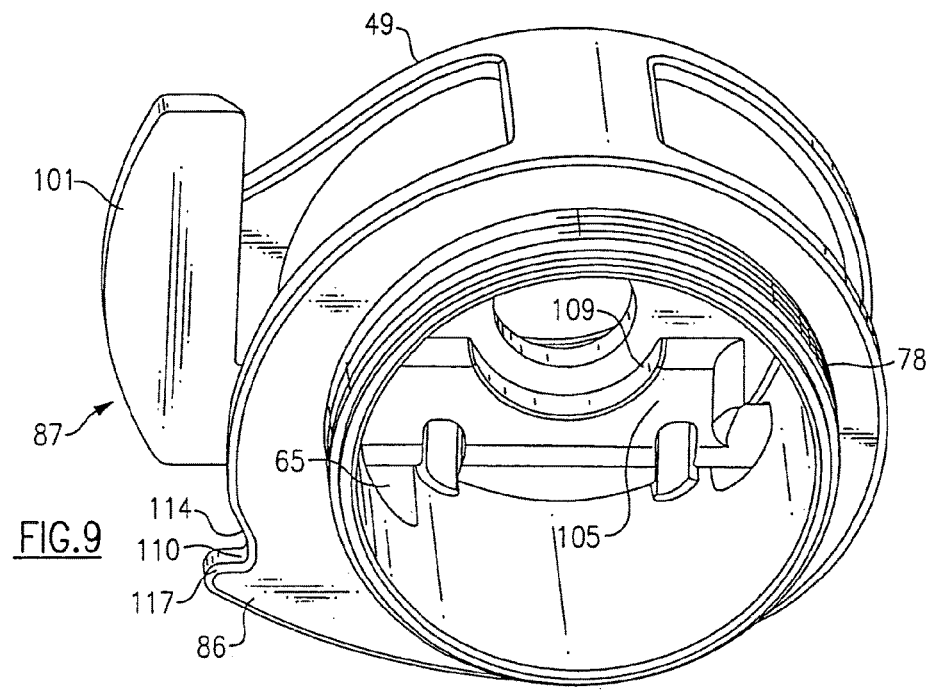
Figure 10:
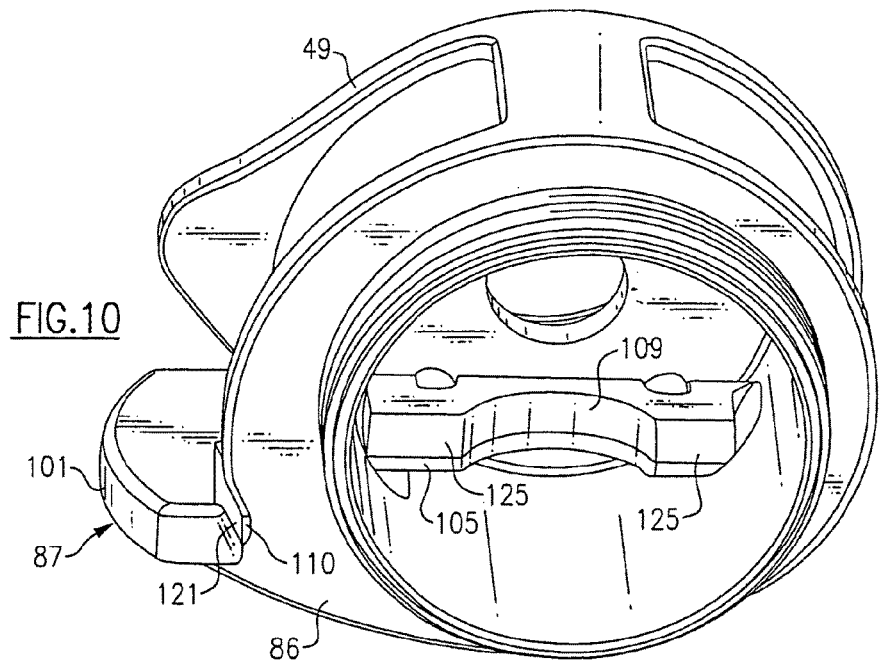
Figure 11:
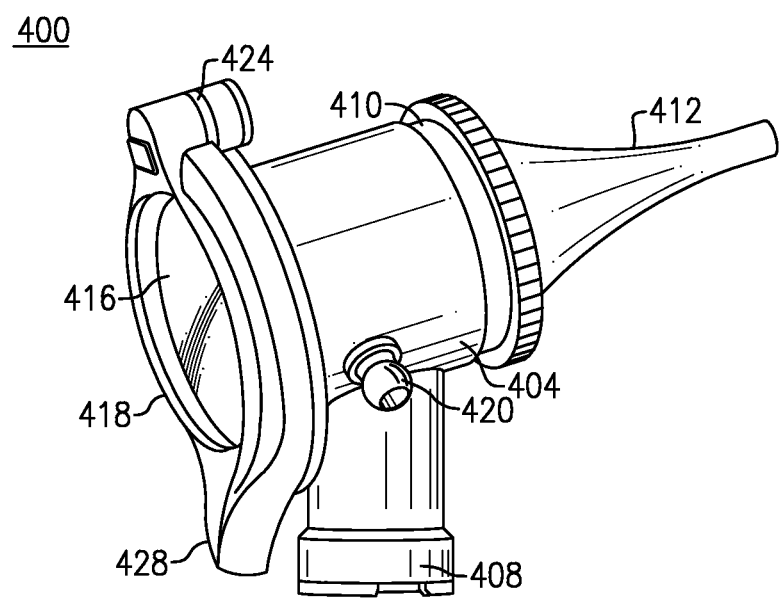
Figure 12:
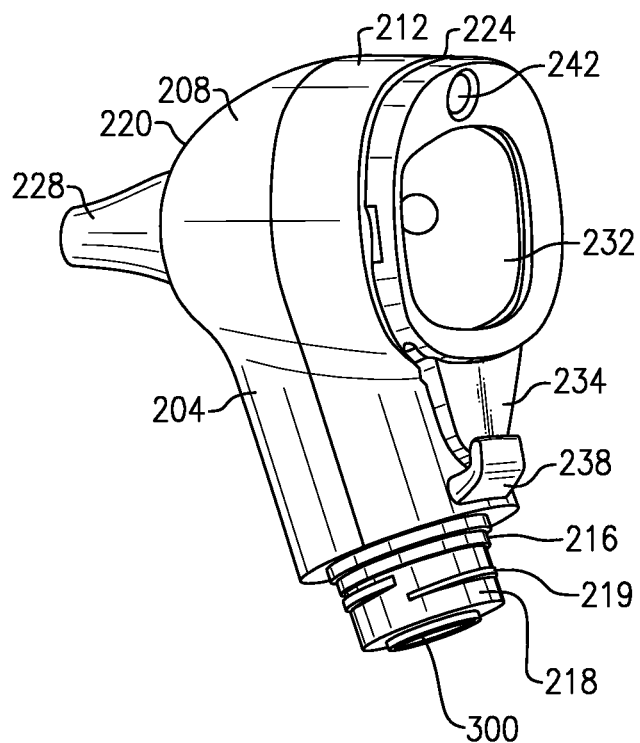
Figure 13:
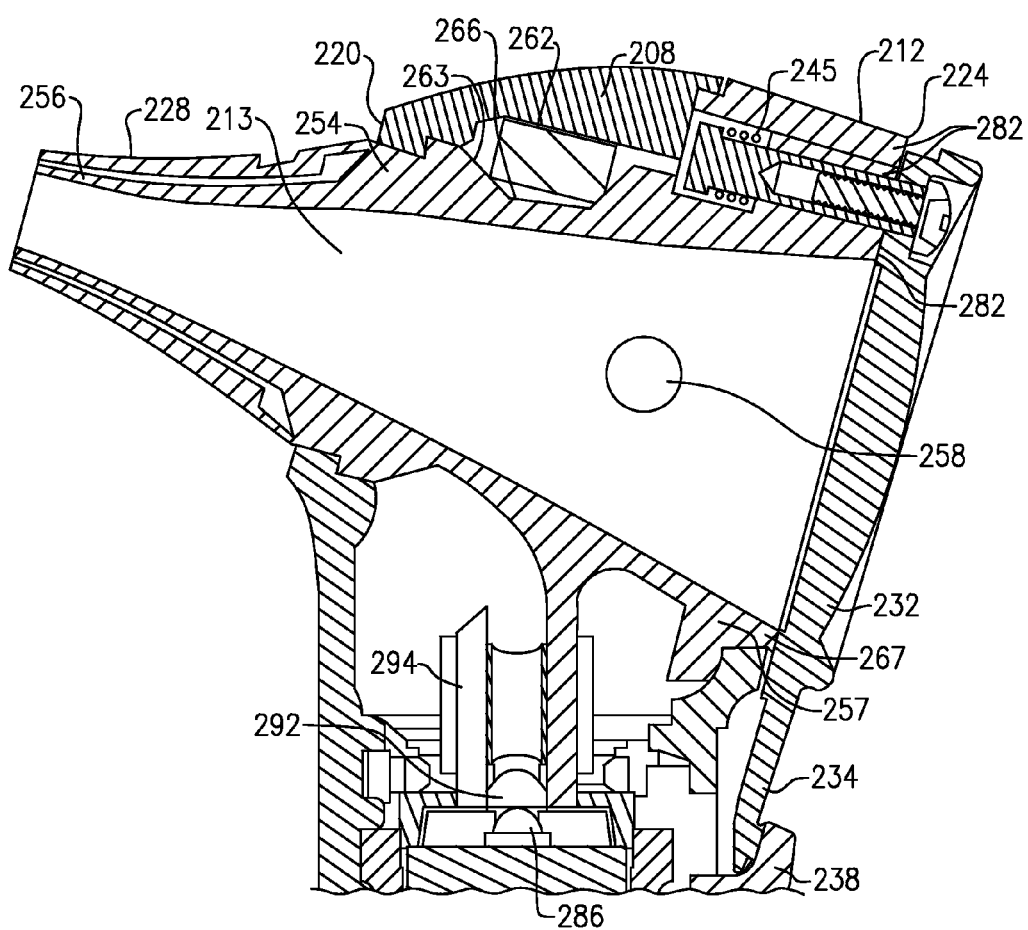
Figure 14:
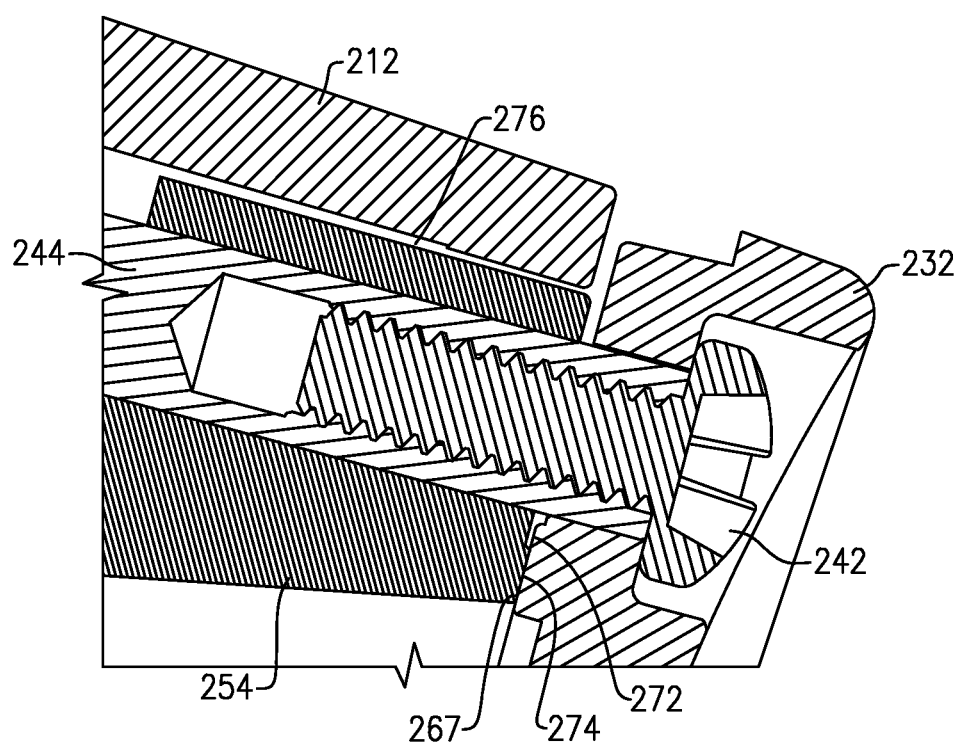
Figure 15:
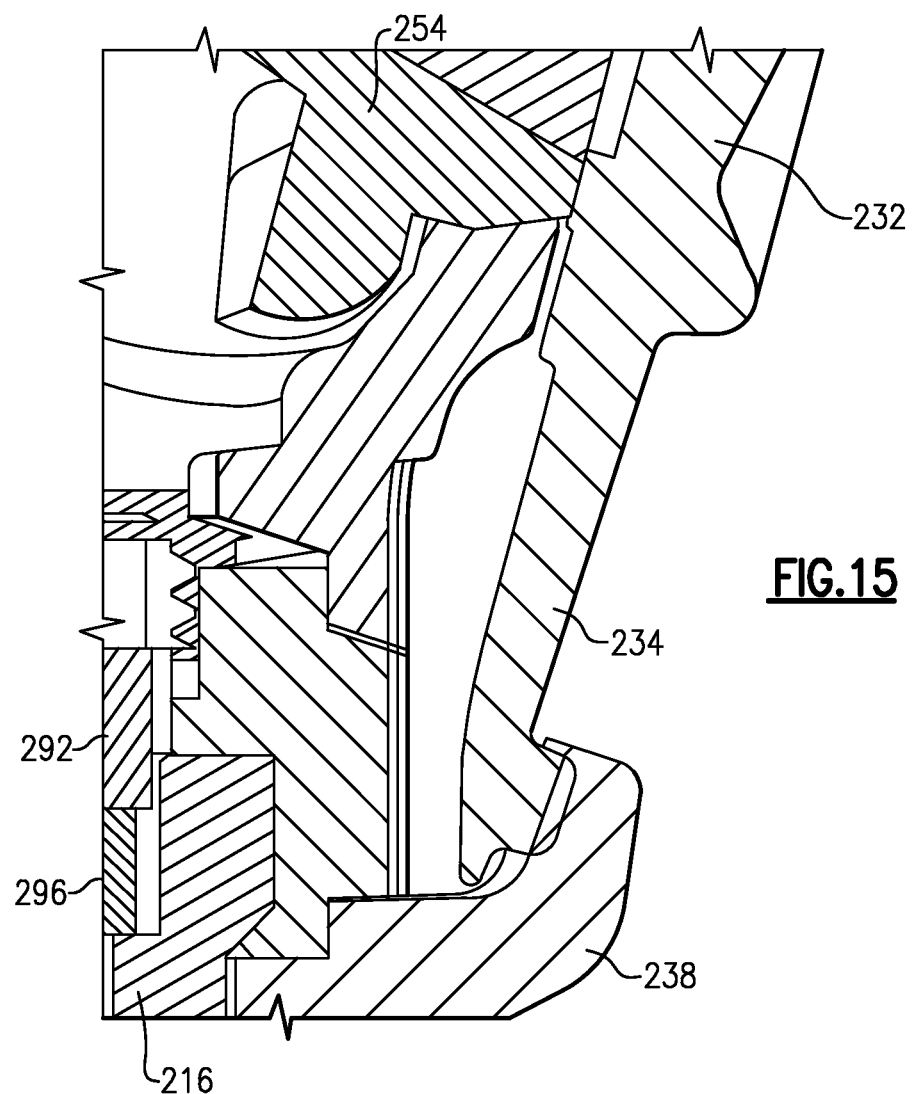
Figure 16:
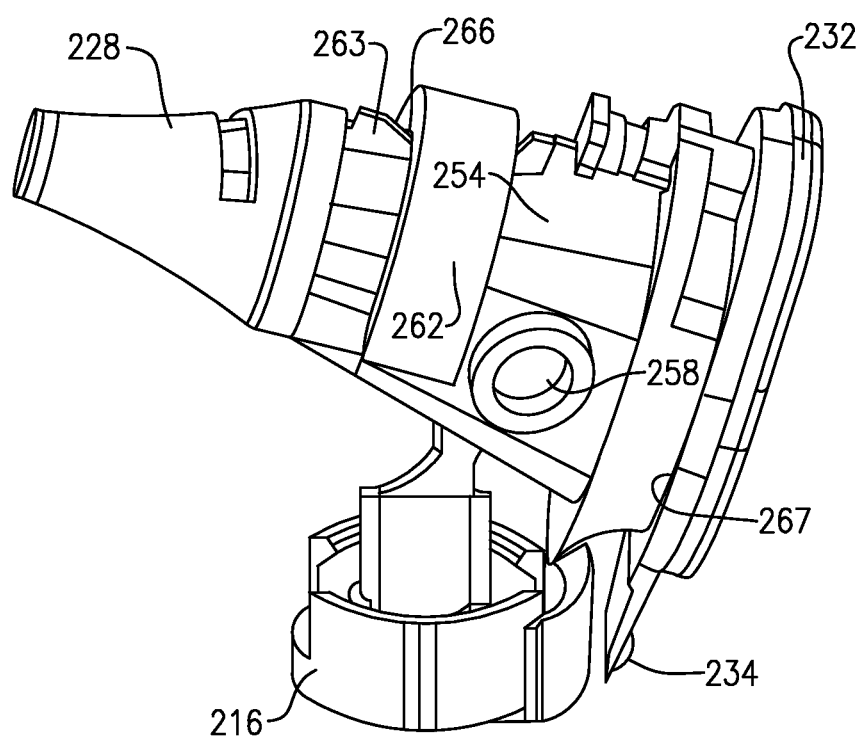

Having thus described the invention in general terms, reference will now be made to the accompanying drawings, which are not necessarily drawn to scale, and wherein:

FIG. 1 is a top perspective view of a compact medical diagnostic instrument in accordance with a first embodiment;

FIG. 2 is an exploded view of the medical diagnostic instrument of FIG. 1;

FIG. 3 is a side view, taken in section, of the medical diagnostic instrument of FIGS. 1 and 2 showing a switch assembly in accordance with one aspect of the invention in a closed or "ON" position;

FIG. 4 is a partial top view of the medical diagnostic instrument of FIG. 3:

FIG. 5 is the side sectioned view of the medical diagnostic instrument showing the switch assembly of FIGS. 3 and 4 in an open or "OFF" position;

FIG. 6 is an enlarged partial view of FIG. 5;

FIG. 7 is a side sectioned view of a compact medical diagnostic instrument having a switch assembly in accordance with a second embodiment, the switch assembly being shown in a closed or "ON" position;

FIG. 8 is a side sectioned view of the medical diagnostic instrument of FIG. 7, with the switch assembly being shown in the open or "OFF" position;

FIGS. 9 and 10 are partial bottom perspective views of a top cap portion of the instrument of FIGS. 1-6, FIG. 9 showing the switch assembly in the "ON" position, and FIG. 10 showing the switch assembly in the "OFF" position;

FIG. 11 is a perspective view of a prior art pneumatic otoscope;

FIG. 12 is a side perspective view of a an instrument head according to yet another embodiment;

FIG. 13 is a side section view of the instrument head of FIG. 12;

FIG. 14 is an enlarged view of a portion of the side section view of FIG. 13 showing, in part, where a viewing lens attaches to the instrument head using a retaining screw;

FIG. 15 is another enlarged view of a portion of the side section view of FIG. 13 showing, in part, where a lens tab attaches to a tab holder of the instrument head and the formation of an effective dynamic seal; and FIG. 16 is a side perspective view of the instrument head of FIG. 12 with the housing removed.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout for purposes of clarity and applicability.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although a number of specific terms are employed herein, these terms are used in a generic and descriptive sense only and not for purposes of limitation, except where so specifically indicated.

The following description relates to certain embodiments of a medical diagnostic instrument having a mechanical switch assembly and other features as described for a specific type of instrument (e.g., an otoscope). As will become apparent from the discussion, however, the inventive concepts can easily be applied to literally any form or instrument design that includes a light source and at least one contained battery. Moreover, certain terms are used throughout the discussion, such as "top", "bottom", "above", "below", "upward", "downward", and the like that are used to provide a frame of reference with regard to the accompanying drawings. These terms, however, should not be interpreted as limiting in the sense of the scope of the invention, except where specifically indicated.

Referring to FIGS. 1-6, a compact medical diagnostic instrument is shown, herein labeled by reference numeral 30. As noted for purposes of each of the following embodiments, the herein described instrument 30 is an otoscope, used for examining the outer ear, including the tympanic membrane. The instrument 30 includes a handle 34 and an instrument head 43 that is releasably attached to the top of the handle 34. According to this depicted embodiment, the handle 34 is substantially cylindrical in shape and is defined by a hollow tubular section having a pair of open ends 37, 39 forming an interior 41 that includes a battery compartment that is sized and configured to retain a pair of vertically stacked batteries 45. In this embodiment and to provide better perspective in combination with the accompanying drawings, a pair of AA batteries 45 are retained within the handle 34.

The instrument 30 further includes a top cap portion 49 and a bottom cap portion 53 sized for covering each of the open ends 37, 39, of the hollow handle 34, respectively. In the depicted version, each of the cap portions 49, 53 are attached by means of screw threads 78, 58 that engage with mating internal threads 42, 46 that are formed in each of the open ends 37, 39 of the tubular handle 34, respectively. The handle 34 is sized to be fitted within the palm of the hand of the intended user.

More specifically, the bottom cap portion 53 includes a compression spring 57 fitted within a defined cavity for engaging the lowermost or bottom end of the stacked batteries 45. As noted, this portion 53 includes a set of external screw threads 58 on an open distal end thereof that mate releasably with corresponding internal screw threads 46 provided on the open end 39 of the handle 34.

The top cap portion 49 of the instrument 30 is defined by a substantially hollow member having an upper mating portion 72, a lower mating portion 76 and an intermediate supporting portion 80. The intermediate supporting portion 80 includes an exterior surface 60 that receives a fitted pocket clip 63 comprising a cylindrical band 64 and a vertically extending clip member 68 permitting the compact instrument 30 to be easily carried, for example, within the shirt pocket of the user. The exterior surface 60 of the intermediate supporting portion 80 further includes a vertically extending slot 65 that is sized to accommodate a portion of a movable member 87 of a mechanical switch assembly in accordance with the invention, as described in greater detail below.

The upper mating portion 72 is a tubular cylindrical section having a diameter that is smaller than that of the remainder of the top cap portion 49, the upper mating portion 72 further including a set of external screw threads 74. The lower mating portion 76 also includes a set of screw threads 78 and is sized to directly engage the internal screw threads 42 of the open top end 37 of the handle 34, wherein the lower mating portion 76 is positioned within the handle when assembled thereto. Each of the top and bottom cap portions 49, 53 are made from an electrically conductive metal, such as stainless steel or a die cast zinc alloy. The handle 34 according to this version is made from an extruded metal, such as aluminum or brass.

The instrument head 43 includes a housing 59 having a frusto-conical insertion portion 61 provided on a distal end that is sized for receiving a disposable speculum (not shown) permitting insertion thereof to a predetermined distance into the ear canal. The insertion portion 61 includes a defined distal tip opening 66 encircled with a ring of light transmitting ends (not shown) from a bundle of optical fibers (not shown), the bundle extending through the substantially hollow exterior of the instrument head 43 in proximity to a contained lamp assembly 69 installed at the base of the head 43. The head 43 further includes a magnifying eyepiece 73 that is mounted on a proximal end 77 along a defined optical path aligned with the distal tip opening 66. An opening (not shown) is also defined in one of the sides of the instrument head 43 for inclusion of a pneumatic or other pressurized source (not shown) for insufflation of a patient's ear during examination. It should be noted that the overall design and features of the otoscopic instrument head, as described in this paragraph, are commonly known to those in the field and require no further discussion, except where needed, in regard to the present invention.

The lamp assembly 69, FIG. 3, is defined by an assembly housing 75 made from a conductive material, such as brass or stainless steel, and contains a light source in the form of a miniature incandescent lamp 81 positioned within a defined cavity 85, FIG. 5, thereof. The lamp assembly 69 further includes an electrical contact 89 at a proximal end 93 thereof. Such lamp assemblies are described, for example, in U.S. Pat. No. 4,147,163, and are commonly known, the assemblies themselves not forming an essential part of the invention. Alternatively, other types of miniature light sources are within the intended scope of the invention, including LEDs.

In this embodiment, the lamp assembly 69 is fixedly attached to the base of the instrument head 43 in a vertical orientation, such that the electrical contact 89 projects downwardly therefrom and the glass envelope of the lamp 81 is positioned at the top extending from the distal end of the assembly housing 75. The instrument head 43 further includes a set of internal screw threads 103 that engage with the external screw threads 74 provided on the upper mating portion 72 of the top cap portion 49, permitting releasable assembly thereto. When fully assembled, a through opening of the top cap portion 49 permits the top (e.g., the cathode) of the contained batteries 45 to make electrical contact with the extending electrical contact 89 of the lamp assembly 69. As previously noted, the contained batteries 45 are biased into contact with the electrical contact 89 of the lamp assembly 69 by means of the compression spring 57 located in the bottom cap portion 53. In passing, it should be noted that the lamp assembly 69, though described as being part of the instrument head 43, could alternately be attached directly to the top cap portion 49.

As shown in FIGS. 4 and 6, the mechanical switch assembly according to this embodiment, consists of the movable member 87. In at least one version, the movable member 87 is fabricated from a non-conductive material, such as plastic, that is made via a low cost manufacturing process, such as injection molding. The movable member 87 is installed through the vertical slot 65 formed in the intermediate supporting portion 80 of the top cap portion 49. The slot 65 is then substantially covered and the movable member 87 is effectively retained by the cylindrical band 64 of the pocket clip 63. The portion 99 of the movable member 87 extending into the top cap portion 49 is pivotally attached therein and is retained, by means of ribs 97.

The movable member 87 further includes an extending or exterior lever portion 101 that can be rotated between a first or OFF position and a second or ON position by the user. According to the depicted embodiment, the top cap portion 49 includes a pair of stop plates 86, 88, FIG. 1, to prevent over rotation of the movable member 87 in either direction by the user, the stop plates 86, 88 being arranged relative to the exterior lever portion 101. The portion 99 of the movable member 87 extending into the top cap portion 49 includes a flap 105, the flap 105 having a center cutout or recess 109 for avoiding the battery contact. In addition, detent features are provided such that the movable member 87 can be secured in the OFF position, as shown more particularly in FIGS. 9 and 10. In the depicted version, the lower stop plate 86 includes a pocket 110 at the predetermined end of travel of the movable member 87, the pocket 110 being defined by a downwardly ramped surface 114 extending into a retaining surface 117. The exterior lever portion 101 includes a beveled surface 121 that permits release of the movable member 87 from the defined pocket 110 of the stop plate 86 upon sufficient finger force by the user. In addition, a beveled surface 125 is also similarly provided on a leading edge of the flap 105 for creating an overcenter engagement with the top of the stacked batteries 45, FIG. 2.

As shown, the threads of the instrument head 43 and the mating top cap portion 49 are designed in terms of their overall length and pitch such that, when assembled, the insertion portion 61 is juxtaposed relative to the movable member 87. That is, the eyepiece 73, in the case of the instrument head 43, is directly above the exterior lever portion 101 of the movable member 87.

In operation, the lamp 81 is energized when the exterior lever portion 101 is in the ON position of FIGS. 3, 4 and 9 in which the electrical contact 89 of the lamp assembly 69 is in electrical connection with the top of the batteries 45. The compression spring 57 provides sufficient biasing force for the circuit to be completed, wherein the instrument handle 34 is made from a conductive material, such as metal, as it provides a continuous electrical path. The use of the compression spring 57, as described herein, also compensates for small differences between battery lengths without impacting performance.

Rotation of the exterior lever portion 101 of the movable member 87, in this instance, using a clockwise direction by the user, as shown by arrows 102, FIG. 2, causes the engagement end 99 to pivot and causes the flap 105 to push the stacked batteries 45 against the biasing force supplied by the compression spring 57. This action thereby creates a gap between the stacked batteries 45 and the electrical contact 89 at the proximal end of the assembly housing 75, as shown most clearly in FIGS. 5, 6 and 10. As noted above, the exterior lever portion 101 is drawn over the stop plate 86 and into the defined pocket 110, wherein the ramped surface 114 provides a detent, thereby securing the movable member 87 in this position. In the meantime, the beveled surface 125 at the leading edge of the flap 105 also creates positive engagement with the top of the stacked batteries 45. In this OFF position for the instrument 30, as shown in FIGS. 5 and 6, the battery contact is disconnected directly from the electrical contact 89 of the lamp assembly 69.

Typically known hand-held diagnostic instruments utilize a metal top cap. To insure the tight tolerances, this part is typically machined from a material such as brass. The handle of the instrument is also typically made from brass, and more typically plated machined brass. Because of the relative lack of complexity afforded the instrument of the present invention, these components can be fabricated using a metal die cast process (for the top cap) or extruded aluminum (for the handle), thereby providing a substantial cost reduction. The metal die cast process is similar to injection molding, in that a hard tool is created and the material is injected in a molten state in order to fill the tool. The resulting product of manufacture is a high tolerance, very repeatable part. This same process can be utilized to make parts for any other diagnostic instrument utilizing the present invention. To our knowledge, metal die cast bases are currently not utilized in diagnostic products today.

Referring to FIG. 2, another novel aspect of the present invention includes the utilization of a printed plastic graphic sleeve member 100 to visually enhance the look of the instrument 30. Most products today have an external "look" of machined metal (smooth, knurled, etc.) or plastic (ribs, smooth, etc.). A proposed solution to this problem is to use commercial "shrink sleeves" that can incorporate multi-colored printed graphics. Images can include both text and graphics, covering literally any content, ranging from corporate logos, photographs, sports themes, etc. It is believed this has never been done on any medical diagnostic product (s). In addition, the sleeve member 100 can also include instructions for operating the switch assembly, wherein the instructions or other information can be written in any language, thereby customizing the instrument for use anywhere in the world.

A number of alternative embodiments to the switch assembly 83 of FIGS. 1-6 are conceivable. Examples of such embodiments are herein briefly described.

As shown in FIGS. 7 and 8, a mechanical switch assembly 130 in accordance with a second embodiment is herein described. For purposes of clarity, those features that are substantially similar to those of the preceding embodiment are labeled with the same reference numerals. In this example, a diagnostic instrument similarly includes a substantially cylindrical hollow handle 34 and an instrument head 43, as in the preceding, wherein a pair of batteries 45 are retained in a stacked configuration within the interior 41 of the hollow handle 34. A lamp assembly 69 is positioned relative to the top of the handle 34, or as in this embodiment, the lamp assembly 69 is fixedly disposed in the bottom of the instrument head 43. The lamp assembly 69 includes a light source, such as a miniature incandescent lamp or other emitting source.

The switch assembly 130 according to this embodiment includes a movable pin-like member 134 having an angled wedge portion or section 138 at one end. The pin-like movable member 134 is movable within aligned openings that are provided in the top cap portion 49 in a direction that is substantially perpendicular to the vertical or battery axis of the instrument.

According to this embodiment, one end of the movable member 134 extends from the exterior of the top cap portion 49 of the handle 34 and is accessible by the user, wherein the angled wedge section 138 can selectively be interposed between the top surface of the upper or topmost battery 45 and the lamp electrical contact 89, thereby creating respective ON and OFF positions. Preferably, the angled wedge section 138 is insulated electrically. As in the preceding and in the absence of the angled wedge section 138, the biasing force of the compression spring 57 is sufficient to create necessary engagement between the electrical contact 89 of the lamp assembly 69 and the batteries 45. Features similar to the detent features described in the preceding embodiment can be added to insure positive engagement in one or both of the ON and OFF positions.

As noted, the preceding describes various examples of switch assemblies and it is anticipated that other similar approaches could be contemplated for moving either one or both of the batteries and/or the lamp assembly.

Moreover, it should be pointed out that the location of the herein described switch assembly can easily be varied. For example, a lever or other movable element (not shown) made in accordance with the inventive concepts discussed herein could be alternatively be provided that breaks the electrical connection at the bottom of the instrument handle. Furthermore, all movements described herein have related to those of the stacked batteries. It should be readily apparent that similar mechanisms could be developed for moving the lamp assembly in lieu of the batteries to selectively break electrical contact or that each of the batteries and the lamp assembly can be made movable relative to one another.

As noted, the preceding instrument included an otoscopic instrument head, but other instrument heads can be similarly attached to the handle 34. By way of a nonlimiting example, an ophthalmoscopic head (not shown) can be attached in lieu of an otoscopic head.

With reference to FIGS. 12-16, there is depicted a medical diagnostic instrument in accordance with another embodiment. More specifically, the instrument 200 herein described is an otoscope used for examining the ears of a patient, and more specifically a pneumatic otoscope. Insufflation (or pneumatic otoscopy) is accomplished by providing, for example, any useful air or gas through an insufflation port preferably located on a portion of an exterior housing wherein the insufflation port permits access to an interior space of the device 200 in communication with an interior of the innerformer, and an interior of the distal insertion portion.

The otoscope 200 is defined by an instrument head 204 that is releasably and securably attached to the upper end of a handle (partially shown in FIGS. 12, 13 and 15). The instrument head 204 according to this version comprises a pair of housings; namely, a front housing 208 and a rear housing 212, each being a shell-like component made from a moldable plastic material. When assembled to one another, the front and rear housings 208, 212 define an enclosure having an inner cavity or interior 213 as well as front (distal) and rear (proximal) ends 220, 224, in which each end further includes a defined opening. A distal insertion portion 228 extends outwardly from the distal end 220 of the assembled instrument head 204, the insertion portion 228 being configured and shaped to support a speculum tip element (not shown) that is suitably sized for insertion into the ear to a predetermined depth.

A viewing lens 232, including a magnifying optic, is attached to the proximal end 224 of the instrument head 204. In one version, the viewing lens 232 is manufactured as a single component that is pivotally attached to the proximal end 224 of the instrument head 204 and more specifically to the rear housing 212, the latter having a rear or proximal opening that is aligned with the smaller front opening of the instrument 200, as well as openings in the distal insertion portion 228 and attached speculum tip element (not shown) to enable viewing of the ear by a caregiver. When assembled, the viewing lens 232 is sized to fully cover the rear opening of the instrument head 204. Optionally, the viewing lens 232 can include a peripheral bumper (not shown). As best shown in FIGS. 13 and 14, the viewing lens 232 is mounted to the instrument head 204 according to this specific embodiment by means of a retaining screw 242 inserted through a hollow swivel pin 244 can be supported by the rear housing 212, the swivel pin 244 and retaining screw 242 being biased by a coil spring 245. When assembled, the viewing lens 232 can rotate about an axis created by the retaining screw 242 and swivel pin 244 so as to selectively cover and uncover the rear opening of the instrument head 204 for access to the interior of the instrument 200, as needed, by a caregiver.

As shown most clearly in FIGS. 13 and 16, the distal insertion portion 228 is attached to one end of an innerformer 254, the latter forming a contained sub-structure of the instrument head 204 that is configured and sized to fit within substantially the entire interior of the instrument head 204. The innerformer 254 can be made as a single component fabricated from a moldable plastic or other suitable material. More specifically, the innerformer 254 is defined by respective distal and proximal ends 256, 257, in which the distal insertion portion 228 is attached to the distal end 256, the latter having a defined opening that is aligned with an opening of the distal insertion portion 228. The innerformer 254 is further defined by a rear opening and peripheral rear surface 267 that are substantially coplanar with the rear opening at the proximal end of the instrument head 204 when the innerformer 254 is assembled. An insufflation port 258 extends outwardly from one lateral side of the innerformer 254 and more specifically through an opening provided in the rear housing 212 to enable access by a caregiver. The specific location of the insufflation port 258 can be varied, provided that the port 258 enables fluid connectivity with the hollow interior of the instrument head 204.

When assembled, the exterior surface of the innerformer 254 engages the interior surfaces of the front and rear housings 208, 212 as well as an attachment portion 218 at the lower end of the instrument head 204. In this assembled position, the peripheral rear surface 267 of the innerformer and an inner peripheral surface 272 of the viewing lens 232 form a junction 274 that defines a seal. According to this specific embodiment, a conformal member (also referred to as a cushion member 262), is attached to an external surface portion of the innerformer 254. The cushion member 262 according to this specific embodiment is a contoured section of urethane foam, such as Poron™ that is adhesively attached to the exterior of the innerformer 254 for engaging an interior surface of the front housing 208.

As discussed herein, the cushion member 262 added to the innerformer 254 helps ensure the device 200 can maintain a pneumatic seal to facilitate insufflation by a clinician. In a version, the innerformer 254 can include a set of guides 263 that define a recess 266 to facilitate the placement/positioning of the cushion member 262. Alternatively, the cushion member 262 can be integrated with the innerformer 254. In use the cushion member 262 acts as a spring that can absorb impact loads and urges the innerformer 254 toward the rear of the instrument 200, as herein described.

That is, the innerformer 254 having the attached cushion member 262 acts to basically "float" within the confines of the instrument head 204 with the innerformer 254 being disposed within the front and rear housings 208, 212 and having a defined space based on the compressibility of the attached cushion member 262 in which the innerformer 254 can move. As shown in the enlarged FIG. 14, a gap or spacing 276, FIG. 14, is created between the innerformer 254 and the rear housing 212. The cushion member 262, when wrapped around the exterior portion of the innerformer 254, helps to locate the innerformer 254 within the confines of the instrument head 204, yet permits movement in response to applied loads or impact forces. The cushion member 262 further functions as a balancer against the lens tab 234 as supported by the tab holder 238. That is, and when the lens tab 234 applies a force to the innerformer 254 and more specifically the rear peripheral surface 267 thereof, the entire innerformer 254 being an single supported section rocks or pivots slightly within the interior of the instrument head 204. As a result, the cushion member 262 deflects and the associated forces that are created against the interior of the instrument head 204 resist the rocking. This resistive force balances the force applied by the lens tab 234 within the lens tab holder 238. If the lens force relaxes due to mechanical creep or other time dependent phenomenon, the cushion member 262 will act to bias the innerformer 254 toward the lens tab 234 and thus help restore the sealing force of the innerformer 254 and more specifically the force applied by the rear peripheral surface 267 against the inner peripheral surface 272 of the viewing lens 232, maintaining the seal at the defined junction 274. The above arrangement has an additional advantage in that it helps compensate for part (tolerance) variation. If the lens tab dimensions vary such that they would produce excess deflection, the cushion member 262 will deflect an additional amount and thus limit the effect of this variation. Prior art devices having rigid innerformers that fail to provide a floating configuration as described herein do not possess this capability. In those cases and at a minimum, excess lens tab forces created due to part variation would compromise any prior formed seal.

In the embodiments illustrated in FIGS. 12-16 and as previously noted, the seal that is formed in the interior chamber of the otoscope 200 due to the herein described "floating" innerformer configuration can stay intact to at least 1 inches of $H_2O$ (1.866 mm Hg) and preferably to at least 2 inches of $H_2O$ (3.732 mmHg) or more.

With further review to FIGS. 12-16, the instrument head 204 includes an attachment mechanism 216 at its lower or bottom end. The attachment mechanism 216 includes a substantially cylindrical portion 218 having a plurality of external threads 219 that are configured to engage a set of internal threads (not shown) formed in the upper end of a handle (not shown). In addition, the attachment mechanism 216 retains an illumination assembly, the latter being fully integrated within the instrument head 204 unlike prior art instruments in which the illumination assembly, typically a miniature incandescent bulb used as a light source, is retained within a necked portion (not shown) of the handle. The illumination assembly according to this embodiment includes an LED 286 disposed within the cylindrical portion 218 of the attachment mechanism 216 and an LED lens assembly 292 and printed circuit board 296 interconnecting the assembly components. According to this embodiment, the LED lens assembly 292 and the printed circuit board 296 are commonly provided in a receptacle 294 (partially shown in FIG. 15) that is disposed and sized to fit within or align with a lower or bottom part of the innerformer 254 using a threaded or other suitable form of connection. When assembled, the LED 286 and the LED lens assembly 292 are aligned with one another along a defined illumination axis and are further aligned with the polished end of a bundle of optical fibers (not shown) also provided in the receptacle 294. The bundle of optical fibers are directed by the innerformer 254 wherein the fibers further extend between the distal end of the innerformer 254 and the distal insertion portion 228.

The illumination assembly components are further connected to a switch (not shown) on the handle of the instrument 200 for purposes of energization. A polarity protection component 300, FIG. 12, is associated with the bottom of the attachment mechanism 216 and relative to a stacked configuration of batteries (not shown) disposed within the handle of the instrument 200.

PARTS LIST FOR FIGS. 1-16

30 compact medical diagnostic instrument
34 handle
37 open end
39 open end
41 interior
42 internal threads
43 instrument head
45 stacked batteries
46 internal threads
49 top cap portion
53 bottom cap portion
57 compression spring
58 external screw threads
59 housing
60 exterior surface
61 insertion portion
63 pocket clip
64 cylindrical band
65 vertically extending slot
66 distal tip opening
68 vertically extending clip member
69 lamp assembly
72 upper mating portion
73 magnifying eyepiece
75 housing, lamp assembly
76 lower mating portion
77 proximal end
78 screw threads
80 intermediate supporting portion
81 miniature incandescent lamp
83 switch assembly
85 cavity
86 stop plate
87 movable member
88 stop plate
89 electrical contact
93 proximal end, lamp assembly
97 ribs
99 portion, movable member
100 graphic sleeve member
101 exterior lever portion
103 internal screw threads
105 flap
109 cutout or recess
110 pocket
114 downwardly ramped surface
117 retaining surface
121 beveled surface
125 beveled surface
130 mechanical switch assembly
134 movable pin-like member
138 angled wedge portion or section
150 otoscope
154 instrument head
158 distal end
162 proximal end
166 speculum
170 lens assembly
174 bumper
200 instrument
204 instrument head 208 front housing
212 rear housing
216 attachment mechanism
218 cylindrical portion
219 external threads
220 distal end
224 proximal end
228 distal insertion portion
232 lens, viewing
234 lens tab
238 lens tab holder
242 retaining screw
244 swivel pin
245 coil spring
254 innerformer
256 distal end, innerformer
257 proximal end, innerformer
258 insufflation port
262 conformal member (cushion member)
263 guides, innerformer
266 recess, innerformer
267 peripheral rear surface, innerformer
272 inner peripheral surface, viewing lens
274 sealing junction (viewing lens/innerformer
276 gap
286 LED
292 LED lens assembly
294 receptacle
296 printed circuit board
300 polarity protection component
400 pneumatic otoscope
404 instrument head
408 attachment end
410 distal insertion portion
412 speculum tip element
416 viewing lens
418 peripheral bumper, viewing lens
420 insufflation port
424 connection
428 lens tab It will be readily apparent that the embodiments described herein are examples for purposes of relating and conveying the inventive concepts. As a result, other variations and modifications are readily discernible that embody these concepts, and as further defined by the following claims.

The invention claimed is:

1. A diagnostic instrument comprising:
 a handle;
 an instrument head associated with the handle, the instrument head comprising a housing that includes a tab holder;
 an innerformer disposed in an inner cavity of the instrument head;
 a cushion member disposed between the innerformer and an interior of the housing; and
 a lens attached to the instrument head, the lens including a lens tab,
  wherein a seal is formed between the lens and the innerformer when the lens tab is engaged with the tab holder.

2. The diagnostic instrument of claim 1, wherein the seal can withstand a pressure of about 1" H$_2$O.

3. The diagnostic instrument of claim 1, wherein the seal can withstand a pressure of about 2" H$_2$O.

4. The diagnostic instrument of claim 1, wherein an interference fit exists when the lens tab is engaged with the tab holder.

5. The diagnostic instrument of claim 1, wherein the innerformer includes an insufflation port extending outwardly from the instrument head.

6. The diagnostic instrument of claim 5, wherein the instrument is a pneumatic otoscope.

7. The diagnostic instrument of claim 1, further comprising a gap between the innerformer and the housing.

8. The diagnostic instrument of claim 1, wherein the instrument is an otoscope.

9. The diagnostic instrument of claim 1, further comprising a light source associated with one of the instrument head and the handle.

10. The diagnostic instrument of claim 9, wherein the light source comprises at least one LED.

11. The diagnostic instrument of claim 9, wherein the light source is retained within an illumination assembly and in which the illumination assembly is retained within an attachment mechanism of the instrument head.

12. The diagnostic instrument of claim 1, in which the innerformer and the instrument head each include a rear opening and in which the innerformer includes a rear surface that engages the lens and creates a seal therebetween.

13. The diagnostic instrument of claim 12, wherein the cushion member biases the rear surface of the innerformer into contact with the lens for maintaining the seal therebetween.

14. A method of manufacturing a handheld diagnostic instrument comprising:
 providing a handle;
 providing an instrument head associated with the handle, the instrument head comprising a tab holder;
 providing an innerformer disposed in an inner cavity of the instrument head;
 providing a cushion member disposed between the innerformer and the housing; and
 providing a lens attached to the instrument head, the lens including a lens tab,
  wherein a seal is formed between the lens and the innerformer when the lens tab is engaged with the tab holder.

15. The method of claim 14, further comprising:
 providing a light source associated with at least one of the handle and the instrument head.

16. The method of claim 15, wherein the light source is one of a miniature incandescent bulb and at least one LED.

17. The method of claim 14, wherein the cushion member is adhesively attached to the innerformer.

18. A method of conducting pneumatic otoscopy with a handheld otoscope comprising:
 providing an otoscope, the otoscope comprising;
  an instrument head associated with a handle, the instrument head having a housing, wherein the housing comprises a tab holder;
  an insertion portion at a distal end of the instrument head;
  an innerformer disposed in an inner cavity of the instrument head;
  a cushion member disposed between the innerformer and the housing; and
  a lens attached to the instrument head, the lens including a lens tab,
   wherein a seal is formed between the lens and the innerformer when the lens tab is engaged with the tab holder;
 inserting the insertion portion into an ear canal of a patient; and inserting a gas into the inner cavity of the instrument head through an insufflation port located on a portion of the instrument head, wherein the gas passes through the inner cavity, through the insertion portion, and to the ear canal.

19. The method of claim 18, wherein the cushion member is disposed relative to the housing to cause the innerformer to be biased toward the lens.

20. The method of claim 18, wherein the cushion member is made from an compliant material.

\* \* \* \* \*